US009649384B2

(12) United States Patent
Banov

(10) Patent No.: US 9,649,384 B2
(45) Date of Patent: *May 16, 2017

(54) NATURAL SOLUBILIZER AGENT COMPRISING A SYNERGISTIC BLEND OF HEPTYL GLUCOSIDE AND OLIVE OIL GLYCERETH-8 ESTERS FOR TRANSDERMAL COMPOSITIONS

(71) Applicant: Daniel Banov, Sugar Land, TX (US)

(72) Inventor: Daniel Banov, Sugar Land, TX (US)

(73) Assignee: Professional Compounding Centers of America, Houston, TX (US)

( * ) Notice: Subject to any disclaimer, the term of this patent is extended or adjusted under 35 U.S.C. 154(b) by 67 days.

This patent is subject to a terminal disclaimer.

(21) Appl. No.: 14/682,317

(22) Filed: Apr. 9, 2015

(65) Prior Publication Data

US 2016/0296625 A1    Oct. 13, 2016

(51) Int. Cl.
| | | |
|---|---|---|
| *A61K 31/56* | (2006.01) | |
| *A61K 47/26* | (2006.01) | |
| *A61K 31/566* | (2006.01) | |
| *A61K 47/14* | (2017.01) | |
| *A61K 31/568* | (2006.01) | |
| *A61K 9/00* | (2006.01) | |

(52) U.S. Cl.
CPC ............ *A61K 47/26* (2013.01); *A61K 9/0014* (2013.01); *A61K 31/566* (2013.01); *A61K 31/568* (2013.01); *A61K 47/14* (2013.01)

(58) Field of Classification Search
CPC ...... A61K 31/56; A61K 31/57; A61K 31/565; A61K 31/575
See application file for complete search history.

(56) References Cited

U.S. PATENT DOCUMENTS

2011/0311592 A1* 12/2011 Birbara ................. A61K 8/498
424/400

OTHER PUBLICATIONS

Sepiclear G7TM, Septic Feb. 2014.*
Resplanta, safety datasheet, Jan. 2010.*
"Olivatis 15"; Technical Data Sheet; Medolla Cosmetic Speciality Ingredients; distributed by: CoastSouthwest.

* cited by examiner

*Primary Examiner* — Jean Cornet
(74) *Attorney, Agent, or Firm* — Gable Gotwals; David G. Woodral

(57) ABSTRACT

The present disclosure refers to a synergistic blend of heptyl glucoside and olive oil derivatives, which is included as a natural solubilizer agent in transdermal compositions to improve API solubilization. Improved solubilization of APIs increases the absorption of APIs into the patient's bloodstream resulting in desired levels of hormones. Reduction of the amount of APIs within the transdermal compositions to achieve the desired levels of hormones will reduce symptoms of hormone deficiency. The synergistic blend within transdermal compositions functions as a solubilizer agent, which allows complete dissolution of hormones, improves water solubility and increases skin permeation. Hormones that can be used in transdermal compositions comprising the synergistic blend include systemically active hormones, which are delivered through the skin with the assistance of natural solubilizer agents and skin penetration enhancers to achieve a desired effect.

9 Claims, No Drawings

NATURAL SOLUBILIZER AGENT COMPRISING A SYNERGISTIC BLEND OF HEPTYL GLUCOSIDE AND OLIVE OIL GLYCERETH-8 ESTERS FOR TRANSDERMAL COMPOSITIONS

CROSS REFERENCE TO RELATED APPLICATIONS

N/A

BACKGROUND

Field of the Disclosure

The present disclosure relates generally to pharmaceutical compositions, and more particularly, to natural solubilizer agents within transdermal pharmaceutical compositions for the delivery of hormones.

Background Information

The delivery of active pharmaceutical ingredients s (APIs) through a biological surface (e.g., skin tissue) is a well-recognized method of treatment for controlled drug delivery. Such APIs are delivered to the surface of the skin of a patient with transdermal delivery through the skin occurring thereafter.

Transdermal drug delivery is receiving increased attention due to the ability of an administration regime to provide a controlled route for the release of an API into the systemic circulation of the patient. The delivery of drugs (e.g., hormones) using transdermal methodology provides many benefits as compared to other delivery methods, such as, for example topical, oral, injection, and the like. Primarily, transdermal delivery is a comfortable, convenient and non-invasive way of administering drugs. Issues with other drug delivery methods include, for example, the variable rates of absorption of APIs in each metabolism encountered when using oral treatments (e.g., in oral hormones), and other inherent inconveniences, such as, gastrointestinal irritation.

Transdermal delivery is a particularly advantageous delivery route. It is a non-invasive drug delivery method with the benefits of better patient compliance, less risk of infection, and lower cost than invasive procedures such as injection and implantation. Transdermal delivery also provides a much shorter onset time (i.e., the time from administration to therapeutic effect) than oral delivery does. Transdermal applications of APIs are simple and can be administered by a caregiver or the patient with minimal discomfort.

Some APIs, such as, hormones (e.g., estrogens, androgens, and other sex hormones), are derived from a kind of fat called cholesterol. Their lipid-based origin makes hormones fat or lipid soluble, but prevents hormones from freely dissolving in water (water insoluble). Since blood plasma (the liquid part of blood that carries hormones to tissues and cells throughout the body) is about 90 percent water, hormones have trouble in mixing with and traveling into the blood. When using transdermal applications for the delivery of hormones, it is difficult to obtain desired treatment outcomes with preferred dosage levels of hormones because of the relatively lower water solubility and lower skin permeation properties. Transdermal application formulations including hormones require high loads of hormones or large application surface areas in order to provide desired hormone levels in the blood.

The lower solubility and relatively lower permeability of many APIs with diverse physicochemical characteristics can be improved using chemical enhancement means. Issues with most known chemical solubilizers and penetration enhancers include, for example, that they are often toxic, irritating, or allergenic. Improving APIs solubility may result in the decrease or elimination of penetration enhancers and thereby result in APIs becoming more available, and hence, more effective for a given dose.

Accordingly, there is a need for solubilizer agents in transdermal pharmaceutical compositions for hormone delivery, which can improve solubilization of hormones, thereby increasing skin permeation.

SUMMARY

The present disclosure refers to natural solubilizer agents to improve hormones solubilization. The natural solubilizer agents are used in transdermal compositions for the delivery of hormones to increase hormone levels in the bloodstream of a patient and reduce symptoms of hormone deficiency. Natural solubilizer agents comprise a synergistic blend of (1) a compound produced from the catalytic reaction of glucose and a castor oil derivative with (2) an olive oil derivative. The natural solubilizer agents improve the skin penetration of APIs. In an example and described below, the compound produced from the catalytic reaction of glucose and the castor oil derivative (e.g., heptanol) is heptyl glucoside (e.g., SEPICLEAR G7™). In this example, the olive oil derivative is implemented as olive oil glycereth-8 esters (e.g., OLIVATIS 15™).

In some embodiments, diseases or conditions that can be treated by using transdermal compositions comprising natural solubilizer agents include testosterone replacement therapy, female hormone replacement therapy (e.g., post-menopausal condition), androgen replacement therapy in females (e.g., lack of libido), amongst others.

The natural solubilizer agents comprising the synergistic blend are particularly useful in transdermal administration of hormones. In some embodiments, hormones that can be used in transdermal compositions comprising natural solubilizer agents include systemically active hormones that are delivered through the skin with the assistance of the natural solubilizer agents to achieve a desired effect.

In some embodiments, heptyl glucoside is a 1biobased non-ionic surfactant, a concentrated O/W solubilizer, easily biodegradable and free of ethoxylated oils. In these embodiments, heptyl glucoside enables the introduction of hydrophobic compounds into aqueous medium. In these embodiments, heptyl glucoside is a natural alkyl glycoside and a hydrotrope that improves solubility of active pharmaceutical ingredients (APIs), thereby enhancing skin permeability to APIs.

In some embodiments, olive oil glycereth-8 esters is a 1biobased water soluble emulsifier having improved emollient and lubricant properties, and easily biodegradable. In these embodiments, olive oil glycereth-8 esters is miscible in oil and can dissolve natural oils even at low concentrations.

In other embodiments, the amount of natural solubilizer agents included within transdermal compositions ranges from about 10% w/w to about 99% w/w. In these embodiments, natural solubilizer agents provide more efficient API solubilization, thereby improving skin permeation. Further to these embodiments, natural solubilizer agents allow lower API dosage requirements.

In some embodiments, natural solubilizer agents comprising the synergistic blend of heptyl glucoside and olive oil glycereth-8 esters, allow a complete dissolution of the APIs, improves water solubility, and increases skin permeation.

According to some embodiments, natural solubilizer agents comprising heptyl glucoside and olive oil glycereth-8 esters are used in the formulation of transdermal compositions. In these embodiments, transdermal compositions include different components, such as APIs, suitable additives, amongst others. Further to these embodiments, APIs are pharmacologically active hormones.

In some embodiments, transdermal compositions comprising natural solubilizer agents include: heptyl glucoside in an amount of from about 10% w/w to about 60% w/w; olive oil glycereth-8 esters in an amount of from about 40% w/w to about 90% w/w; and APIs in an amount of from about 0.5% w/w to about 10% w/w.

In other embodiments, transdermal compositions comprising natural solubilizer agents include one or more olive oil derivatives such as polyglyceryl-3 olivate phosphate, polyglyceryl-3 pentaolivate, polyglyceryl-3 cetearyl ether olivate, and the like. In these embodiments, olive oil derivatives are in an amount of from about 40% w/w to about 90% w/w.

In some embodiments, various additives are included to facilitate the preparation of suitable dosage forms. For example, additives include diluents, thickening agents, transdermal absorption enhancers, pH adjusters, preservatives, colors, stabilizing agents, antioxidants, and surfactants, amongst others.

In some embodiments, transdermal compositions comprising natural solubilizer agents are manufactured in a range of dosage forms, such as, a liquid, cream, paste, gel, lotion, patch (matrix and reservoir), tape, plaster or film former. In the more preferred embodiment, transdermal pharmaceutical compositions are in the form of a liquid for application to a defined area of skin.

In other embodiments, transdermal pharmaceutical compositions comprising natural solubilizer agents are manufactured in any form suitable for topical application to the skin. Suitable forms include sprayable liquids, gels, liquids that may be applied using a roll-on device, lacquers, and sustained release matrices of transdermal delivery devices such as patches. Transdermal pharmaceutical compositions are usually administered alone but, under some circumstances, administration can be accomplished by using other delivery mechanisms, such as, iontophoresism, ultrasound and microneedles to enhance penetration.

In some embodiments, the patient to be treated with transdermal compositions comprising natural solubilizer agents is generally a mammal, preferably a human being, male or female.

In other embodiments, transdermal compositions comprising natural solubilizer agents are used to deliver a therapeutically effective amount of the APIs to a local area or to the systemic circulation. In these embodiments, transdermal compositions provide a pharmaceutically effective level of the API in the systemic circulation, for example, a pharmaceutically effective level of API within the bloodstream.

In some embodiments, low dose APIs in any of the above identified dosage forms can result in acceptable hormone levels in the patient. This contrasts with current popular topical treatment options, which use high dosages of hormones to get a few milligrams of hormones absorbed into the bloodstream of the patient.

In other embodiments, transdermal compositions comprising natural solubilizer agents are preferably applied in a dose sufficient to provide an effective amount of the at least one API in the bloodstream of the patient.

In some embodiments, the dosages (e.g., daily) required depend on the type of hormone included in the transdermal compositions comprising natural solubilizer agents. In other words, some hormones are more potent than others, and hence, the dosing can vary among the various hormones used.

Numerous other aspects, features, and benefits of the present disclosure may be made apparent from the following detailed description

DETAILED DESCRIPTION

The present disclosure is here described in detail. Other embodiments may be used and/or other changes may be made without departing from the spirit or scope of the present disclosure. The illustrative embodiments described in the detailed description are not meant to be limiting of the subject matter presented here.

Definitions

As used here, the following terms have the following definitions:

"Active Pharmaceutical Ingredients (APIs)" refer to chemical compounds that induce a desired effect, and include agents that are therapeutically or prophylactically effective.

"Absorption Enhancer" or, equivalently, "Penetration Enhancer" refers to a substance used to modify, generally to increase, the rate of permeation through skin or other body tissue of one or more substances (e.g., APIs) in a formulation.

"Biobased" refers to materials or products that are composed in whole, or in significant part, of biological products or renewable agricultural materials, or forestry materials.

"Treating" and "Treatment" refers to reduction in severity and/or frequency of symptoms, elimination of symptoms and/or underlying cause, prevention of the occurrence of symptoms and/or their underlying cause, and improvement or remediation of damage.

"Therapeutically effective amount" refers to the amount of the subject compound that will elicit the biological or medical response of a tissue, system, animal or human that is being sought.

"Transdermal drug delivery" refers to administration of a drug to the skin surface of a patient so that the drug passes through the skin tissue and into the patient's blood stream, thereby providing a systemic effect.

"Vehicle" refers to a substance of no therapeutic value that is used to convey at least one API for administration.

Description of the Disclosure

Solubilizer Agents

The present disclosure refers to natural solubilizer agents to improve hormones solubilization. The natural solubilizer agents are used in transdermal compositions for the delivery of hormones to increase hormone levels in the bloodstream of a patient and reduce symptoms of hormone deficiency. Natural solubilizer agents comprise a synergistic blend of (1) a compound produced from the catalytic reaction of glucose and a castor oil derivative with (2) an olive oil derivative. The natural solubilizer agents improve skin penetration of APIs. In an example and described below, the compound produced from the catalytic reaction of glucose and the castor oil derivative (e.g., heptanol) is heptyl glucoside (e.g., SEPICLEAR G7™). In this example, the olive oil derivative is implemented as olive oil glycereth-8 esters (e.g., OLIVATIS 15™)

In some embodiments, diseases or conditions that can be treated by using transdermal compositions comprising natural solubilizer agents include testosterone replacement therapy, female hormone replacement therapy (e.g., post-menopausal condition), androgen replacement therapy in females (e.g., lack of libido), amongst others.

The natural solubilizer agents comprising the synergistic blend are particularly useful in transdermal administration of hormones. In some embodiments, hormones that can be used in transdermal compositions comprising natural solubilizer agents include systemically active hormones that are delivered through the skin with the assistance of the natural solubilizer agents to achieve a desired effect.

In some embodiments and as described in an example above, the compound produced from a catalytic reaction of glucose and a castor oil derivative (e.g., heptanol) is heptyl glucoside (e.g., SEPICLEAR G7™). In these embodiments, heptyl glucoside is a natural alkyl glycoside and a hydrotrope that improves solubility of active pharmaceutical ingredients (APIs), thereby enhancing skin permeability to APIs. Further to these embodiments, heptyl glucoside is expressed by the following formula:

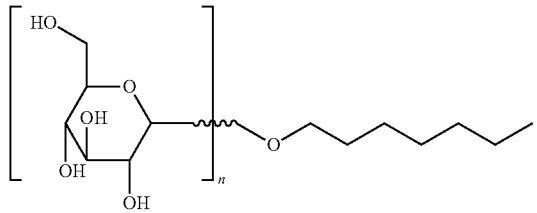

In some embodiments, heptyl glucoside is a 1biobased non-ionic surfactant, a concentrated O/W solubilizer, easily biodegradable and free of ethoxylated oils. In these embodiments, heptyl glucoside enables the introduction of hydrophobic compounds into aqueous medium. Further to these embodiments, heptyl glucoside allows a complete dissolution of the APIs, improves water solubility, and increases skin permeation. Additionally, heptyl glucoside solubilizes lipophilic compounds contained within aqueous media, such as, hormones, essential oils, perfumes, vitamin E, and the like.

In other embodiments and described in an example above, the olive oil derivative is olive oil glycereth-8 esters (e.g., OLIVATIS 15™). In these embodiments, olive oil glycereth-8 esters is obtained by a trans-esterification process where part of the glyceric fraction of olive oil is substituted by ethoxylated vegetal oil. Further to these embodiments, olive oil glycereth-8 esters is expressed by the following formula:

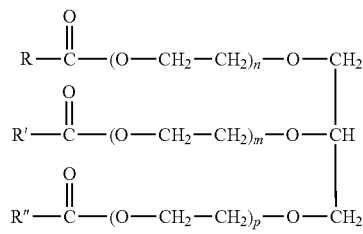

wherein R—CO, R'—CO and R"—CO represent the fatty acids derives from starting olive oil and (n+m+p) has an average value of 8.

In some embodiments, olive oil glycereth-8 esters is a biobased water soluble emulsifier having improve emollient and lubricant properties, and easily biodegradable. In these embodiments, olive oil glycereth-8 esters is miscible in oil and can dissolve natural oils even at low concentrations.

In other embodiments, the amount of natural solubilizer agents included within transdermal compositions ranges from about 10% w/w to about 99% w/w. In these embodiments, natural solubilizer agents provide more efficient API solubilization, thereby improving skin permeation. Further to these embodiments, natural solubilizer agents allow lower API dosage requirements.

In some embodiments, natural solubilizer agents comprising the synergistic blend of heptyl glucoside and olive oil glycereth-8 esters, allow a complete dissolution of the APIs, improve water solubility and increase skin permeation.

APIs

According to some embodiments, natural solubilizer agents comprising heptyl glucoside and olive oil glycereth-8 esters are used in the formulation of transdermal compositions. In these embodiments, transdermal compositions include different components, such as APIs, suitable additives, amongst others. Further to these embodiments, APIs are pharmacologically active hormones.

In some embodiments, suitable pharmacologically active hormones are selected from estrogens, such as, estradiol, estriol, estradiol benzoate, estradiol 17 beta-cypionate, estradiol enanthate, estradiol propionate, estrone, ethinylestradiol, fosfestrol, dienestrol mestranol, stilboestrol, dienoestrol, epioestriol, estropipate diethylstilbestrol, chlorotrianisene, conjugated estrogenic hormones, polyestradiol phosphate and zeranol, and mixtures thereof.

In other embodiments, suitable pharmacologically active hormones are selected from progesterone and progestins, such as, norethisterone, norethisterone acetate, gestodene, levonorgestrel, allylestrenol, anagestone, desogestrel, dimethisterone, dydrogesterone, ethisterone, ethynodiol, ethynodiol diacetate, etonogestrel, gestodene, ethinylestradiol, haloprogesterone, 17-hydroxy-16-methylene-progesterone, 17 alpha-hydroxyprogesterone, lynestrenol, medroxyprogesterone, melengestrol, norethindrone, norethynodrel, norgesterone, gestonorone, norethisterone, norgestimate, norgestrel, levonorgestrel, norgestrienone, norvinisterone, pentagestrone, MENT (7-methyl-19-testosterone); norelgestromin, and trimigestone drospirenone, tibolone, and megestrol, and mixtures thereof.

In some embodiments, suitable pharmacologically active hormones are selected from selective progesterone receptor modulators, such as, asoprisnil, CDB-4124, and mixtures thereof.

In other embodiments, suitable pharmacologically active hormones are selected from selective estrogen receptor modulators, such as, bazedoxifene, clomifene, fulvestrant, lasofoxifene, raloxifene, tamoxifen, toremifene, and mixtures thereof.

In some embodiments, suitable pharmacologically active hormones are selected from antiprogestogen, such as, mifepristone, aglepristone, and mixture thereof.

In other embodiments, suitable pharmacologically active hormones are selected from antigonadotropins, such as, danazol, gestrinone, and mixtures thereof.

In some embodiments, suitable pharmacologically active hormones are selected from antiandrogens, such as, cyproterone acetate, danazol, and mixtures thereof.

In other embodiments, suitable pharmacologically active hormones are selected from antiestrogens, such as, tamoxifen and epitiostanol and the aromatase inhibitors, exemestane and 4-hydroxy-androstenedione and its derivatives, and mixtures thereof.

In some embodiments, suitable pharmacologically active hormones are selected from androgens and anabolic agents, such as, androisoxazole, androstenediol, bolandiol, bolasterone, clostebol, ethylestrenol, formyldienolone, 4-hydroxy-19-nortestosterone, methandriol, methenolone, methyltrienolone, nandrolone, norbolethone, oxymesterone, stenbolone and trenbolone. Androgenic steroids can include boldenone, fluoxymesterone, mestanolone, mesterolone, methandrostenolone, 17-methyltestosterone, 17.alpha.-methyltestosterone 3-cyclopentyl enol ether, norethandrolone, normethandrone, oxandrolone, oxymesterone, oxymetholone, prasterone, stanlolone, stanozolol, testosterone, testosterone 17-chloral hemiacetal, testosterone proprionate, testosterone enanthate tiomesterone dehydroepiandrosterone (DHEA), androstenedione (Andro): an androstenediol, androsterone, dihydrotestosterone (DHT), androstanolone, and derivatives thereof.

In other embodiments, suitable pharmacologically active hormones are selected from 5-alpha reductase inhibitors, such as, finasteride, turosteride, LY-1917nd MK-3, or mixtures thereof.

In some embodiments, suitable pharmacologically active hormones are selected from aromatase inhibitor, such as, aminogluthetimide, anastrozole, exemestane, formestane, letrozole or vorozole.

In other embodiments, suitable pharmacologically active hormones are selected from gonadotropins, such as, clomifene and urofollitropin.

In some embodiments, suitable pharmacologically active hormones are selected from GnRH:(receptor) agonists, such as, buserelin, goserelin, histrelin, leuprorelin, nafarelin and triptorelin.

In other embodiments, suitable pharmacologically active hormones are selected from GnRH antagonist, such as, abarelix, cetrorelix and ganirelix.

In some embodiments, suitable pharmacologically active hormones are selected from pituitary hormones and their active derivatives or analogs, such as, corticotrophin, thyrotropin, follicle stimulating hormone (FSH), luteinising hormone (LH) and gonadotrophin releasing hormone (GnRH).

In other embodiments, suitable pharmacologically active hormones are selected from thyroid hormones, such as calcitonin, thyroxine and liothyronine, and antithyroid agents such as carbimazole and propylthiouracil.

In some embodiments, suitable pharmacologically active hormones are selected from other miscellaneous hormone agents, such as, octreotide; and mixtures from two or more of the groups.

Formulation

In some embodiments, transdermal compositions comprising natural solubilizer agents include heptyl glucoside in an amount of from about 10% w/w to about 60% w/w; olive oil glycereth-8 esters in an amount of from about 40% w/w to about 90% w/w; and APIs in an amount of from about 0.5% w/w to about 10% w/w.

In other embodiments, transdermal compositions comprising natural solubilizer agents include one or more olive oil derivatives, such as, polyglyceryl-3 olivate phosphate, polyglyceryl-3 pentaolivate, polyglyceryl-3 cetearyl ether olivate, and the like. In these embodiments, olive oil derivatives are in an amount of from about 40% w/w to about 90% w/w.

In some embodiments, various additives are included to facilitate the preparation of suitable dosage forms. For example, additives include diluents, thickening agents, transdermal absorption enhancers, pH adjusters, preservatives, colors, stabilizing agents, antioxidants, and surfactants, amongst others.

Administration

In some embodiments, transdermal compositions comprising natural solubilizer agents are manufactured in a range of dosage forms, such as, a liquid, cream, paste, gel, lotion, patch (matrix and reservoir), tape, plaster or film former. In the more preferred embodiment, transdermal pharmaceutical compositions are in the form of a liquid for application to a defined area of skin.

In other embodiments, transdermal compositions comprising natural solubilizer agents are manufactured in any form suitable for topical application to the skin. Suitable forms include sprayable liquids, gels, liquids that may be applied using a roll-on device, lacquers, and sustained release matrices of transdermal delivery devices such as patches. Transdermal pharmaceutical compositions are usually administered alone but, under some circumstances, administration can be accomplished by using other delivery mechanisms, such as, iontophoresism, ultrasound and microneedles to enhance penetration.

In some embodiments, the patient to be treated with transdermal compositions comprising natural solubilizer agents is generally a mammal, preferably a human being, male or female.

In other embodiments, transdermal compositions comprising natural solubilizer agents are used to deliver a therapeutically effective amount of the APIs to a local area or to the systemic circulation. In these embodiments, transdermal compositions provide a pharmaceutically effective level of the API in the systemic circulation, for example, a pharmaceutically effective level of API within the bloodstream.

In some embodiments, low dose APIs in any of the above identified dosage forms can result in acceptable hormone levels in the patient. This contrasts with current popular topical treatment options, which use high dosages of hormones to get a few milligrams of hormones absorbed into the bloodstream of the patient.

In other embodiments, transdermal compositions comprising natural solubilizer agents are preferably applied in a dose sufficient to provide an effective amount of the at least one API in the bloodstream of the patient.

In some embodiments, the dosages (e.g., daily) required depend on the type of hormone included in the transdermal compositions comprising natural solubilizer agents. In other words, some hormones are more potent than others, and hence, the dosing can vary among the various hormones used.

The following examples are intended to illustrate the scope of the disclosure and are not intended to be limiting. It is to be understood that other pharmaceutical formulations know to those skilled in the art may alternatively be used.

EXAMPLES

Example #1 illustrates formula for a transdermal composition comprising natural solubilizer agents and estradiol.

These percentages may refer to % weight by weight, % weight by volume, or % volume by volume.

| FORMULA | |
|---|---|
| INGREDIENTS | COMPOSITION |
| Estradiol | 1.5% |
| Heptyl Glucoside | 20% |
| Olive Oil Glycereth-8 Esters | 78.5% |

Example #2 illustrates formula for a transdermal composition comprising natural solubilizer agents and testosterone.

These percentages may refer to % weight by weight, % weight by volume, or % volume by volume.

| FORMULA | |
|---|---|
| INGREDIENTS | COMPOSITION |
| Testosterone | 5% |
| Heptyl Glucoside | 20% |
| Olive Oil Glycereth-8 Esters | 75% |

Example #3 illustrates formula for a transdermal composition comprising natural solubilizer agents and estriol.

These percentages may refer to % weight by weight, % weight by volume, or % volume by volume.

| FORMULA | |
|---|---|
| INGREDIENTS | COMPOSITION |
| Estriol | 1.5% |
| Heptyl Glucoside | 20% |
| Olive Oil Glycereth-8 Esters | 78.5% |

While various embodiments of the present disclosure have been described above, it should be understood that they have been presented by way of example only, and not limitation. Numerous changes to the disclosed embodiments can be made in accordance with the disclosure herein without departing from the spirit or scope of the disclosure. Thus, the breadth and scope of the present disclosure should not be limited by any of the above described embodiments. Rather, the scope of the disclosure should be defined in accordance with the following claims and their equivalents.

Although the present disclosure has been illustrated and described with respect to one or more implementations, equivalent alterations and modifications can occur to others skilled in the art upon the reading and understanding of this specification and the drawings. In addition, while a particular feature of the disclosure may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A composition for improving hormone solubilization, said composition comprising about 20% w/w heptvl glucoside, an olive oil derivative ester, and at least one active ingredient including at least one steroidal hormone; said heptvl glucoside and said olive oil ester together used to solubilize said at least one steroidal hormone.

2. The composition of claim 1, wherein the olive oil ester is olive oil glycereth-8 esters.

3. The composition of claim 1, wherein the olive oil ester is present in an amount of about 40% w/w to about 90% w/w.

4. The composition of claim 1, wherein the at least one active ingredient including at least one steroidal hormone is present in an amount of about 0.5% w/w to about 10% w/w.

5. The composition of claim 1, wherein the olive oil derivative is selected from the group consisting of polyglyceryl-3 olivate phosphate, polyglyceryl-3 pentaolivate, polyglyceryl-3 cetearyl ether olivate, and combinations thereof.

6. The composition of claim 1, wherein the composition has a form selected from the group consisting of a liquid, cream, paste, gel, lotion, patch, tape, plaster, or combination thereof.

7. A composition for improving hormone solubilization, said composition comprising about 20% w/w heptyl glucoside, olive oil glycereth-8 ester, and at least one active ingredient including at least one steroidal hormone; said heptyl glucoside and said olive oil glycereth-8 ester together used to solubilize said at least one steroidal hormone.

8. The composition of claim 7, wherein the olive oil glycereth-8 esters is present in an amount of about 40% w/w to about 90% w/w.

9. The composition of claim 7, wherein the at least one active ingredient including at least one steroidal hormone is present in an amount of about 0.5% w/w to about 10% w/w.

\* \* \* \* \*